(12) United States Patent
Kaul et al.

(10) Patent No.: US 7,307,170 B2
(45) Date of Patent: Dec. 11, 2007

(54) EPINDOLIDIONE PIGMENTS

(75) Inventors: Bansi Lal Kaul, Biel-Benken (CH); Bruno Piastra, Huningue (FR); Valérie Wolf, Galfingue (FR); Frank Prokschy, Hattersheim (DE); Martin Ulrich Schmidt, Frankfurt (DE)

(73) Assignee: Clariant Finance (BVI) Limited, Tortola (VG)

( * ) Notice: Subject to any disclaimer, the term of this patent is extended or adjusted under 35 U.S.C. 154(b) by 313 days.

(21) Appl. No.: 10/467,041

(22) PCT Filed: Feb. 6, 2002

(86) PCT No.: PCT/IB02/00369

§ 371 (c)(1), (2), (4) Date: Jan. 22, 2004

(87) PCT Pub. No.: WO02/062796

PCT Pub. Date: Aug. 15, 2002

(65) Prior Publication Data

US 2004/0138451 A1 Jul. 15, 2004

(30) Foreign Application Priority Data

Feb. 7, 2001 (GB) .................................. 0103011.3

(51) Int. Cl.
*C07D 471/04* (2006.01)
(52) U.S. Cl. ........................................................ 546/38
(58) Field of Classification Search .................. 546/38
See application file for complete search history.

(56) References Cited

U.S. PATENT DOCUMENTS

| | | | |
|---|---|---|---|
| 4,142,890 A | 3/1979 | Bloom et al. ................ 96/1 PE |
| 5,523,387 A | 6/1996 | Goldmann et al. .......... 534/728 |
| 6,277,536 B1 | 8/2001 | Piastra et al. .................. 430/78 |
| 6,515,123 B2 | 2/2003 | Kaul et al. ..................... 544/74 |

FOREIGN PATENT DOCUMENTS

| EP | 0 766 498 | 4/1997 |
|---|---|---|
| GB | 2 087 419 | 5/1982 |

OTHER PUBLICATIONS

English abstract for JP 10-130554, May 19, 1998.
English abstract for JP 10-189246, Jul. 21, 1998.
English abstract for JP 11-097179, Apr. 9, 1999.
English abstract for JP 11-130972, May 19, 1999.

*Primary Examiner*—Patricia L. Morris
(74) *Attorney, Agent, or Firm*—Vicki L. Sgro

(57) ABSTRACT

The epindolidione compounds of the general formula (I)

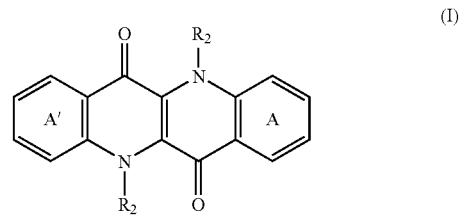

in which A', $R_2$ and A have the meanings given in claim 1, are outstanding pigments which are notable in particular for better migration, light and solvent fastnesses, better heat stability and enhanced colouring power and also better dispersibility and capability to be brought into pigment form.

The invention also relates to a process for preparing these epindolidione compounds and to their use a colorants for colouring polymer compositions or paper pulps, as colorants in electrophotographic toners and developers, as colorants in ink-jet inks, as colorants in the coatings industry, as colorants for textile printing or as a printing ink in the graphical industry, as colorants in cosmetics.

10 Claims, No Drawings

EPINDOLIDIONE PIGMENTS

The invention relates to novel dibenzo[b,g][1,5]naphthyridine-6,12(5H,11H)dione compounds, also called epindolidione compounds, and to their use as pigments. The invention also relates to a particularly advantageous process for preparing these epindolidione compounds.

U.S. Pat. No. 3,334,102 describes the preparation of epindolidione compounds of the following general formula

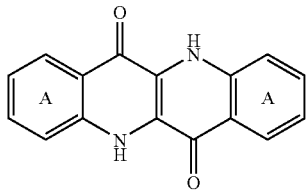

where the rings labelled A carry halogen atoms or methoxy groups.

The preparation process disclosed in U.S. Pat. No. 3,334,102 or in J. Org. Chem., 33(11), 4004 (1968), starts from dimethyl dihydroxyfumarate and simple anilines. The pigments disclosed in U.S. Pat. No. 3,334,102 provide a greenish yellow to reddish yellow shade when applied in polyolefins and lacquers.

It is an object of the invention to provide new orange to red pigments possessing high fastness to solvents, migration and light, which have good thermal stabilities, a high tinting power and are easily dispersible.

Another object of the invention is to provide a process by which the novel pigments are obtainable and which starts from readily available intermediates.

In one of its aspects the present invention provides compounds of the general formula (I)

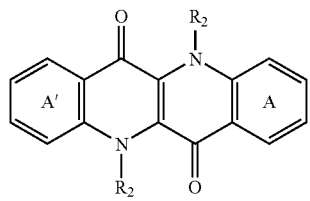

(I)

in which A' represents a substituted or unsubstituted aromatic ring or an annelated heteroaromatic ring system, A represents an annelated heteroaromatic ring system and both $R_2$ are hydrogen, $C_{1-2}$alkyl, phenyl or —COOR, with R being $C_{1-8}$alkyl.

The nucleus designated A comprises an annelated ring which is fused on linearly, in 2,3-position, or angularly, in 1,2- or in 3,4-position, to feature the complementary members of the moieties (1) to (11)

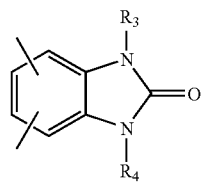
(1)

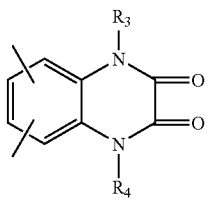
(2)

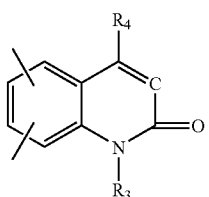
(3)

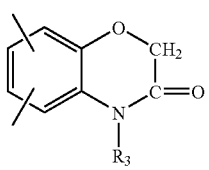
(4)

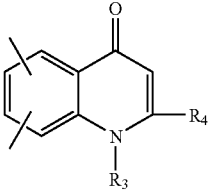
(5)

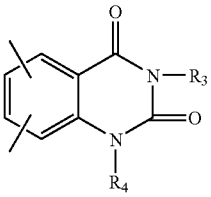
(6)

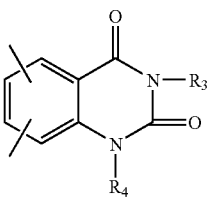
(7)

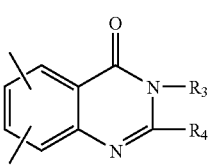
(8)

-continued (9)
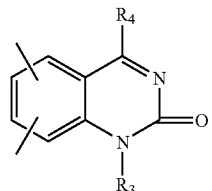

(10)
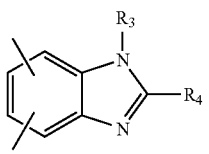

(11)
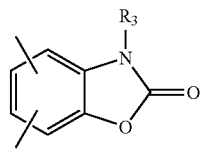

wherein
$R_3$ and $R_4$ are, independently, hydrogen, $C_{1-8}$alkyl, $C_{5-6}$cycloalkyl, benzyl, benzanilide or naphthyl whereby phenyl groups can be mono- or poly-substituted by radicals selected from the group consisting of halogen, nitro groups, $C_{1-8}$alkyl, phenyl, —COOR with R being $C_{1-8}$alkyl, and $C_{1-2}$alkoxy. Preferably, mono- or poly-substitution is by radicals selected from the group consisting of chlorine, $C_{1-4}$alkyl, phenyl and —COOR, with R being $C_{1-8}$alkyl; or $R_3$ and/or $R_4$ are a radical of formula (a)

(a)
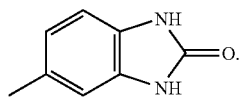

For A' representing an annelated heteroaromatic ring system, the nucleus designated A' comprises an annelated ring which is fused on linearly, in 2,3-position, or angularly, in 1,2- or in 3,4-position, to feature the complementary members of the moieties (12) to (22)

(12)
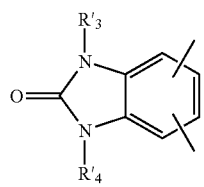

(13)
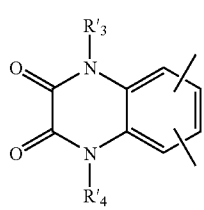

-continued

(14)
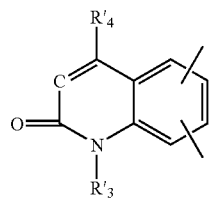

(15)
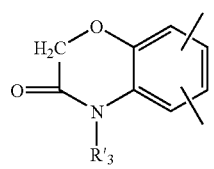

(16)
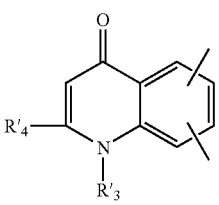

(17)
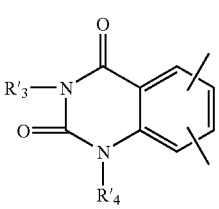

(18)
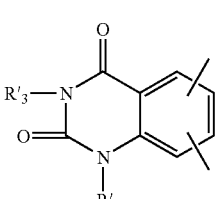

(19)
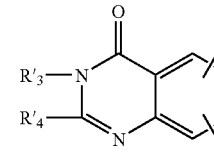

(20)
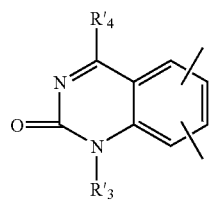

(21)
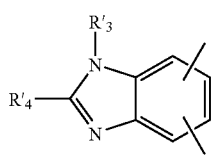

-continued (22)

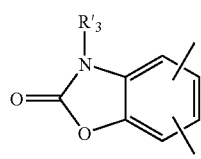

-continued (IIIb)

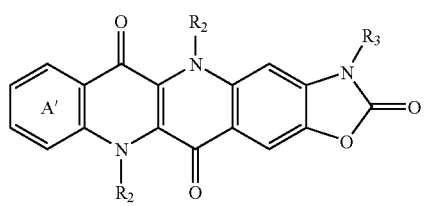

wherein

R'$_3$ and R'$_4$ are, independently, hydrogen, C$_{1-8}$alkyl, C$_{5-6}$cycloalkyl, benzyl, benzanilide or naphthyl whereby phenyl groups can be mono- or poly-substituted by radicals selected from the group consisting of halogen, nitro groups, C$_{1-8}$alkyl, phenyl, —COOR with R being C$_{1-8}$alkyl and C$_{1-2}$alkoxy, Preferably, mono- or poly-substitution is by radicals selected from the group consisting of chlorine, C$_{1-4}$alkyl, phenyl and —COOR, with R being C$_{1-8}$alkyl.

In another aspect the present invention provides compounds of the general formula (I')

(I')

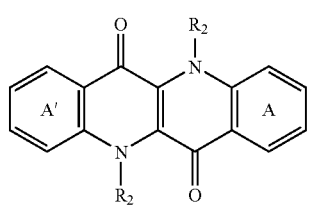

wherein R$_2$, A and A' are defined as above with the exception that R$_3$' and R$_4$' in A' are not hydrogen.

Preferred compounds of formula (I) are those with formulae (Ia), (IIa), (IIIa) and (IIIb)

(Ia)

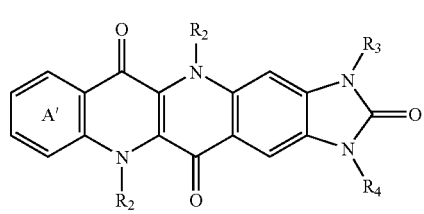

(IIa)

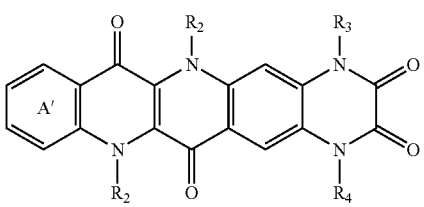

(IIIa)

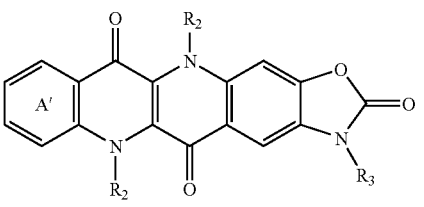

in which A', R$_2$, R$_3$ and R$_4$ are defined as above.

More preferred compounds are those of formula (Ib) and (IIb)

(Ib)

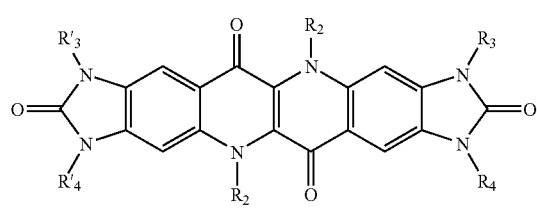

(IIb)

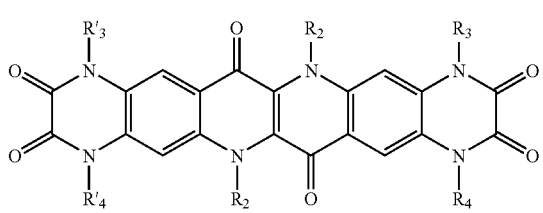

in which R$_2$, R$_3$, R$_4$, R'$_3$ and R'$_4$ are defined as above.

Other more preferred compounds are those of formula (Ic)

(Ic)

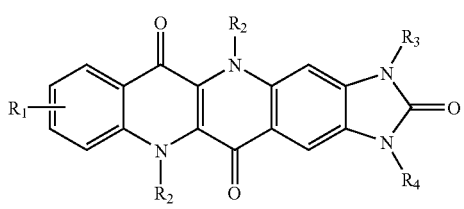

wherein R$_2$, R$_3$ and R$_4$ are defined as above and R$_1$ is hydrogen, halogen or C$_{1-8}$alkyl.

The substituents R$_3$ and R$_4$, independently of one another, are preferably hydrogen, a methyl radical, an ethyl radical, an n- or i-propyl radical, an n-, i-, sec- or tert-butyl radical, a cyclohexyl radical, a substituted or unsubstituted benzanilide radical, a naphthyl radical, a radical of the formula (a)

(a)

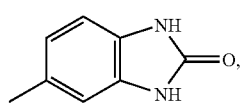

an unsubstituted phenyl radical, a phenyl radical substituted one or more times by halogen, preferably chlorine or nitro groups, phenyl, $C_{1-8}$alkyl, preferably $C_{1-4}$alkyl and $C_{1-2}$alkoxy.

The above mentioned substituted phenyl radical in the definition of $R_3$ or $R_4$ is preferably selected from the group consisting of o-, m-, p-methyl-, ethyl-, chloro-, methoxyphenyl, 2,4- and 3,5-dimethylphenyl, 2,5-dichloro-, dimethoxy-, diethoxy-phenyl, m-, p-nitrophenyl, 2,5-dichloro-, 2,5-diethoxy-4-nitrophenyl, 2-methoxy-4-nitrophenyl, 3-chloro-4-methyl-, 3-chloro-4-methoxyphenyl and p-ethoxyphenyl.

The abovementioned substituted benzanilide radical in the definition of $R_3$ or $R_4$ is preferably selected from the group consisting of radicals of the formulae (b) and (c)

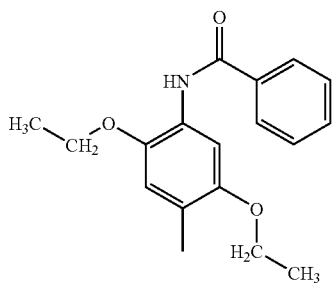

(b)

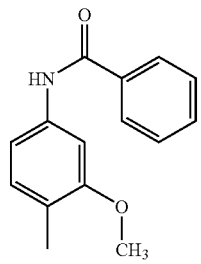

(c)

The substituents $R'_3$ and $R'_4$, independently of one another, are preferably a methyl radical, an ethyl radical, an n- or i-propyl radical, an n-, i-, sec- or tert-butyl radical.

Preferred epindolidione compounds are those for which $R_2$ and $R_4$ are hydrogen and $R_3$ is a methyl, ethyl, propyl or butyl substituent.

Preferred symmetrically tetrasubstituted compounds are the tetramethyl-, tetraethyl-, tetrapropyl (n- or i-) and tetrabutyl (n-, i-, sec- or tert-) substituted compounds.

Another preferred tetrasubstituted compound is the one of formula (Id)

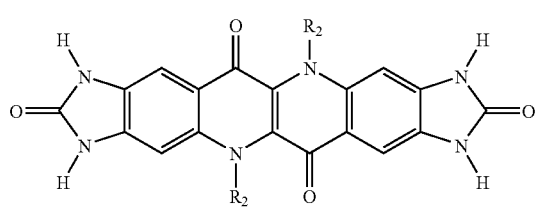

(Id)

wherein $R_2$ is defined as above.

In one aspect, the invention provides a process for preparing epindolidione compounds of the formula (Id) as defined above, characterized by the following reaction path Step 1

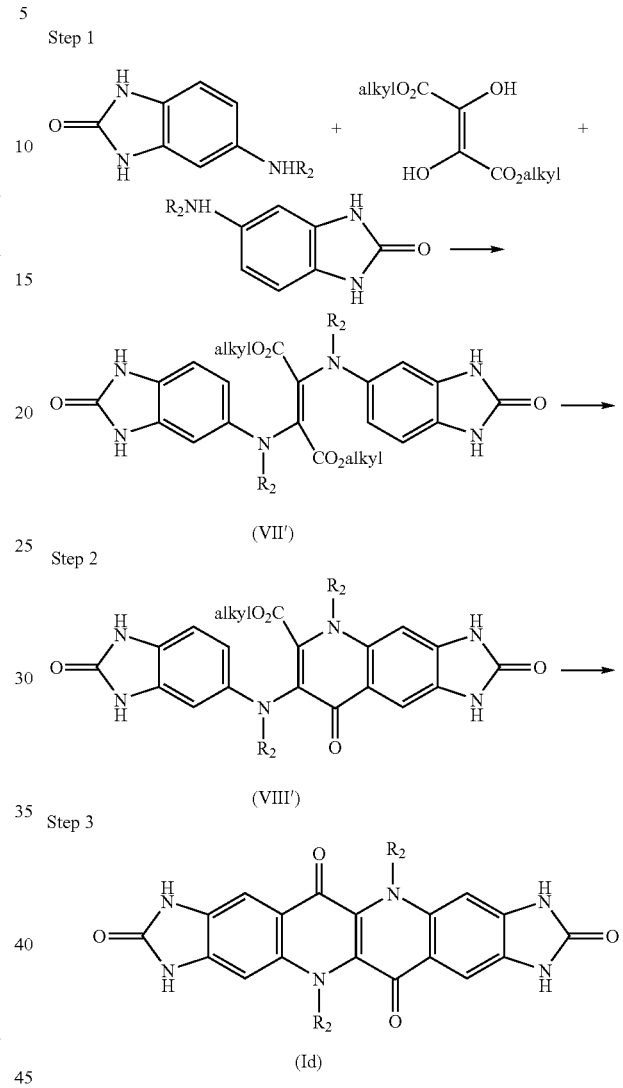

Step 2

(VII')

Step 3

(VIII')

(Id)

The invention further provides a process for the preparation of epindolidione compounds of the formula (I) as described above by the cyclization in polyphosphoric acid or concentrated sulfuric acid of the formula (VIII)

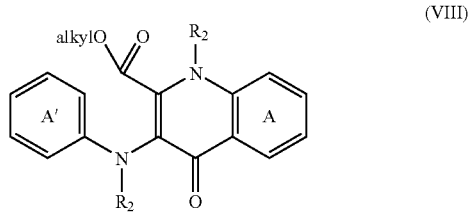

(VIII)

in which A', $R_2$ and A have the meanings given above.

In another aspect the invention provides a process for preparing the epindolidione compounds of formula (I') in which in a first step, an arylamine is condensed with an alkyl chloroacetate or an alkyl bromoacetate in a solvent, in the presence or not of a base acting as a hydrogen chloride or bromide scavenger. The process is carried out in a solvent, e.g. alcohols, toluene, xylene or a xylene mixture, nitrobenzene, chlorobenzene, dimethylformamide, or dimethylacetamide, or N-methylpyrrolidone. The reaction is preferably carried out in ethanol, tert-amyl alcohol or toluene. The reaction temperature is preferably of the order of 10 to 150° C. The base is an inorganic or an organic base selected from common bases used in organic synthesis like sodium acetate, sodium carbonate, sodium or potassium hydroxide or triethylamine.

The arylamine is a compound of the general formula (IV')

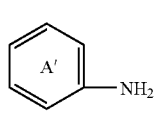

(IV')

in which the nucleus designated A' is defined as above.

Preferred compounds of formula (IV') are aniline or substituted aniline, naphthylamine or substituted naphthylamine or those of formulae (IV'a) to (IV'd)

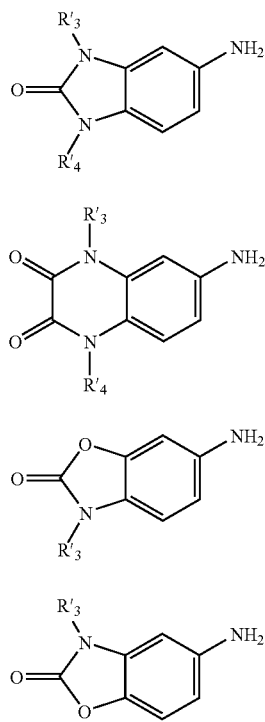

wherein R'$_3$ and R'$_4$ have the meaning as defined above.

The preparation of the compounds of formula (IV'), in particular of formulae (IV'a) to (IV'd), is described in EP 0911337 A.

In a second step of the process, the N-arylglycine alkyl ester is condensed with a dialkyl oxalate in a solvent, in the presence of a strong base. The process is carried out in the same type of solvent as the first step. The reaction is preferably carried out in ethanol, tert-amyl alcohol or toluene. The reaction temperature is preferably of the order of 10 to 150° C. The strong base can be sodium or potassium alcoholate, sodium or potassium hydride, sodium or potassium dialkylamide, or other strong base commonly used in order to prepare carbanions. The strong base is preferably sodium ethoxide, sodium tert-butoxide or sodium tert-amylate. The amount of base is from 1 to 200 mol % based on the N-arylglycine alkyl ester.

Preferably the molar ratio of the N-arylglycine alkyl ester and the dialkyl oxalate is 1:1.

In a third step of the process, the product obtained in step 2 is condensed in a solvent with a compound of the general formula (IV)

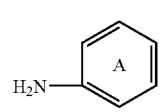

(IV)

in which the nucleus designated A is defined as above.

Preferred compounds of formula (IV) are those of formulae (IVa) to (IVd)

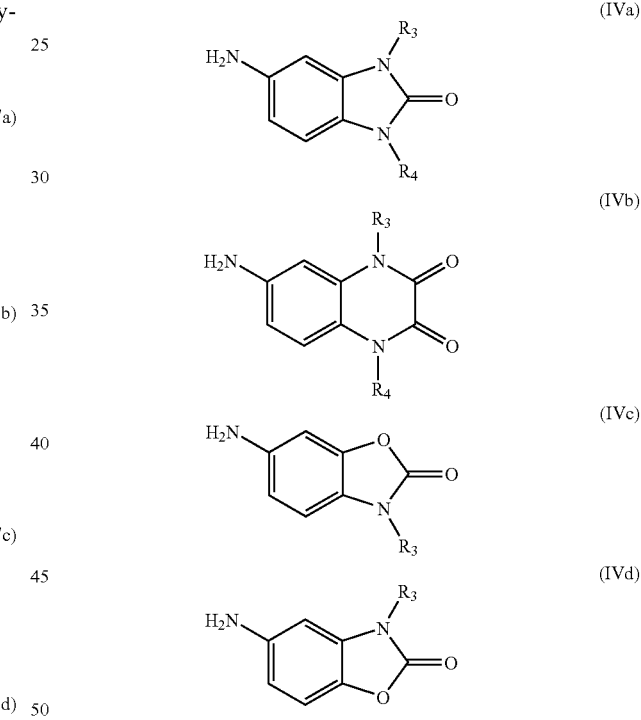

where R$_3$ and R$_4$ have the meaning as defined above.

The preparation of the compounds of formula (IV), in particular of formulae (IV'a) to (IV'd), is described in EP 0911337 A.

The reaction is preferably carried out in ethanol, tert amyl alcohol or toluene. The reaction temperature is preferably of the order of 10 to 200° C. The acid is an inorganic or an organic acid selected from common acids used in organic synthesis such as sulfuric acid, hydrochloric acid, acetic acid or para-toluene sulfonic acid.

In a fourth step of the process, the products (VIIa) and (VIIb) obtained in step 3 are cyclized by heating in an inert high boiling point solvent, in order to give the intermediate (VIII) shown in the flow chart below. The process is carried out in a high boiling point solvent, e.g. diphenyl oxide, mixture of biphenyl and diphenyl oxides also called Dowtherm A or any solvent with a boiling point above 240° C. The reaction temperature is preferably of the order of 200 to 280° C.

Finally, in a fifth step the monocyclized product obtained in step 4 is further cyclized to the epindolidione compound by heating in polyphosphoric acid or conc. sulfuric acid. The reaction temperature is preferably of the order of 100 to 180° C.

A major advantage of this process is that it is possible to easily prepare asymmetrical epindolidione compounds.

The following reaction scheme illustrates the steps of the above described process.

REACTION SCHEME

Step 1

Step 2

Step 3

Step 4

Step 5

To further improve the pigment properties, the crude pigments can be treated in organic solvents at elevated temperatures, for example at from 60 to 200° C., especially from 70 to 150° C. and preferably from 75 to 100° C. Such finishing treatment is preferably combined with a milling or kneading operation.

A further aspect of the invention are the intermediate compounds of formulae (VIIa), (VIIb) and of formula (VIII) as shown in the reaction scheme above.

Epindolidione compounds of the formula (I) according to the invention are in particular useful as pigments.

The pigments according to the invention are suitable for the colouring of polymer compositions, by which are meant solvent-free and solvent-containing compositions comprising plastics or synthetic resins (in oil-based or water-based paints, in coating materials of various kinds, for the spin dyeing of viscose or cellulose acetate, or for pigmenting plastics, such as polyamide, polyethylene, polystyrene, polyvinyl chloride, rubber and artificial leather). They can also be used in printing inks for the graphical industry, for the colouring of paper pulps, for the coating of textile or for pigment printing.

The resulting colorations are notable for their outstanding heat, light and weather fastness, chemical resistance, colour strength and very good applications properties, examples being their crystallization fastness and dispersing fastness, and in particular for their fastness to migration, bleeding, overcoating and solvents.

In addition, the pigments of the invention are also suitable as colorants in electrophotographic toners and developers, such as one- or two-component powder toners (also known as one- or two-component developers), magnetic toners, liquid toners, polymerization toners and further speciality toners.

Typical toner binders are addition polymerization, polyaddition and polycondensation resins, such as styrene, styrene-acrylate, styrene-butadiene, acrylate, polyester and phenolic-epoxy resins, polysulphones, polyurethanes, individually or in combination, and also polyethylene and polypropylene, in or to which further ingredients, such as charge control agents, waxes or flow assistants may be present or may be added subsequently.

A further area of application of pigments of the invention is their use as colorants in powders and powder coating materials, especially triboelectrically or electrokinetically sprayed powder coating materials, which are used to coat the surfaces of articles made, for example, from metal, wood, plastic, glass, ceramic, concrete, textile material, paper or rubber.

Powder coating resins employed are typically epoxy resins, carboxyl- and hydroxyl-containing polyester resins, polyurethane resins and acrylic resins, together with customary hardeners. Combinations of resins are also used. For example, epoxy resins are frequently employed in combination with carboxyl- and hydroxyl-containing polyester resins. Examples of typical hardener components (depending on the resin system) are acid anhydrides, imidazoles and dicyandiamide and derivatives thereof, blocked isocyanates, bisacylurethanes, phenolic and melamine resins, triglycidyl isocyanurates, oxazolines and dicarboxylic acids.

The pigments of the invention are suitable, moreover, as colorants in ink-jet inks, both aqueous and non-aqueous, and in those inks which operate in accordance with the hot-melt process.

The pigments of the invention are also suitable for cosmetics, such as nail varnishes or make-up.

In the following examples the parts and percentages are by weight. The temperatures are indicated in degrees Celsius. One part by volume corresponds to the volume of one part by weight of water.

EXAMPLE 1a 525 parts of aniline are charged in a reactor containing 349 parts of ethyl chloroacetate. The mixture is heated to 80° C. After 20 minutes the reaction starts and the temperature reaches 120° C. within one hour. The temperature decreases slowly and stabilizes to 90° C. after 30 minutes. The reaction mixture is further stirred at 90° C. for 3 hours and then cooled to 50° C. and poured into 875 parts of water. The suspension is filtered, and the solid product is washed with 1000 parts of an alcohol/water (1/9) mixture. It is then washed with water until free of chloride. The product is recrystallized from cyclohexane and dried under reduced pressure at 20° C. to give 310 parts of white cristals of a compound of the following formula

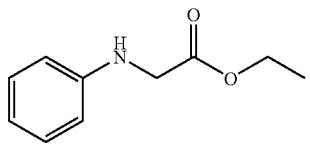

Yield: 62% Melting point: 54.5-55.5° C.

EXAMPLE 1b 35.3 parts of sodium ethoxide are dissolved in 235 parts of ethanol. 69.3 parts of diethyl oxalate are introduced in the reactor and then 84 parts of the product prepared in the example 1a. The mixture is subsequently stirred at 25° C. for 24 hours. The ethanol is then distilled off under vacuum. 352 parts of water and 33 parts of acetic acid are added to the residue under vigorous stirring. 282 parts of toluene are added in order to extract the product. The organic phase is separated from the aqueous phase and washed again with 282 parts of water. The toluene phase is evaporated to give 118.7 parts of a red oil, which is used without further purification in the next step.

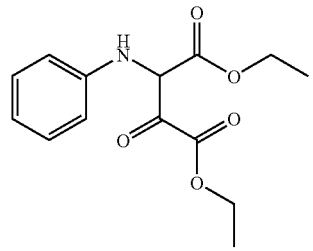

EXAMPLE 1c 110 parts of the product prepared in the example 1b are dissolved in 335 parts of ethanol. 71.4 parts of the following amine

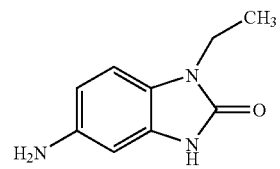

are added to the solution, which is then heated at reflux for 6 hours. The reaction mixture is then cooled to 0° C. with an ice-water bath, filtered and washed with 50 parts of cold ethanol. Drying under reduced pressure at 40° C. gives 44.2 parts of grey powder as a mixture of compounds of the following formula

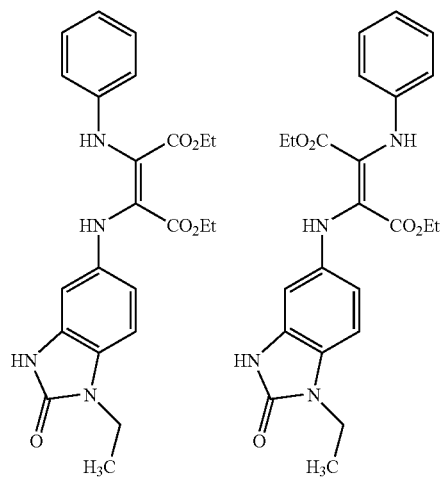

EXAMPLE 1d 22.6 parts of the product prepared in the example 1c are suspended in 30 parts of Dowtherm A and heated at 85° C. to get a solution. This solution is added within 15 minutes to another reactor already charged with 70 parts of Dowtherm A and preheated at 258° C. The ethanol formed during the reaction is distilled off. The reaction mixture is heated at 250° C. for 15 minutes after the end of the addition and then allowed to cool to 25° C. The precipitated product is filtered, washed with 50 parts of Dowtherm A then 700 parts of hexane and dried under reduced pressure at 80° C. This gives 16.6 parts of a brown powder of a mixture of compounds of the following formula

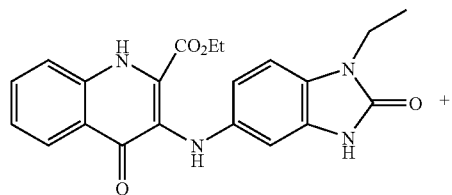

EXAMPLE 1e 16 parts of polyphosphoric acid (85% of $H_3PO_4$ content) and 1.6 part of the product isolated in the example 1d are mixed in a reactor and gradually heated to 150° C. and stirred at this temperature for 4 hours. Then the reaction mixture is cooled to 60° C. and 235 parts of water are added. The suspension is filtered and washed with water. Drying under reduced pressure at 80° C. gives 1.2 part of an orange powder of a compound of the following formula

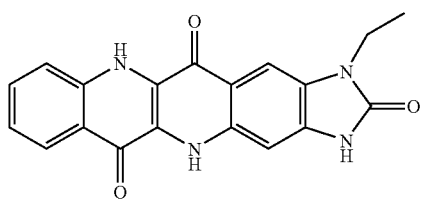

EXAMPLE 2a 639.4 parts of p-chloroaniline are charged in a reactor containing 304 parts of ethyl chloroacetate. The mixture is heated to 80° C. After 20 minutes the reaction starts and the temperature reaches 115° C. within one hour. The temperature decreases slowly and stabilizes to 90° C. after 30 minutes. The reaction mixture is further stirred at 90° C. for 3 hours and then cooled to 50° C. and poured into 300 parts of water and 400 parts of ice. The suspension is filtered, and the solid product is washed with 5000 parts water. It is then washed with water until free of chloride. The product is recrystallized from cyclohexane and dried under reduced pressure at 20° C. to give 346.4 parts of white cristals of a compound of the following formula

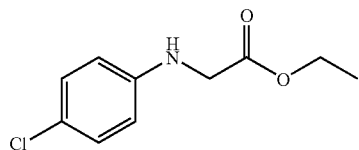

Yield: 67% Melting point: 94-95° C.

EXAMPLE 2b 119.3 parts of sodium ethoxide are dissolved in 800 parts of ethanol. 236 parts of diethyl oxalate are introduced in the reactor and then 341.6 parts of the product prepared in the example 2a. The mixture is subsequently stirred at 25° C. for 24 hours. The ethanol is then distilled off under vacuum. 1200 parts of water and 112 parts of acetic acid are added to the residue under vigorous stirring. 960 parts of toluene are added in order to extract the product. The organic phase is separated from the aqueous phase and washed again with 320 parts of water. The toluene phase is evaporated to give 500 parts of an orange oil, which is used without further purification in the next step.

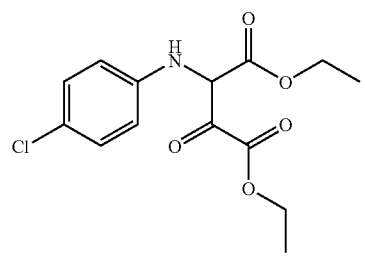

EXAMPLE 2c 487.1 parts of the product prepared in the example 2b are dissolved in 1325 parts of ethanol. 281.4 parts of the following amine

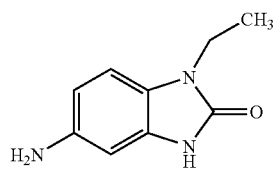

are added to the solution, which is then heated at reflux for 6 hours. The reaction mixture is then cooled to 0° C. with an ice-water bath, filtered and washed with 1000 parts of cold ethanol. Drying under reduced pressure at 40° C. gives 284.6 parts of grey powder as a mixture of compounds of the following formula

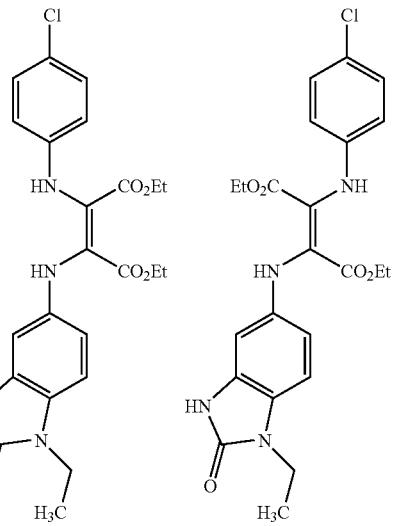

EXAMPLE 2d 100 parts of the product prepared in the example 2c are suspended in 1050 parts of Dowtherm A and heated at 150° C. This solution is added within 15 minutes to another reactor already charged with 787 parts of Dowtherm A and preheated at 258° C. The ethanol formed during the reaction is distilled off. The reaction mixture is heated at 250° C. for 15 minutes after the end of the addition and then allowed to cool to 25° C. The precipitated product is filtered, washed with 150 parts of Dowtherm A then 800 parts of ethanol and dried under reduced pressure at 80° C. This gives 64 parts of a brown powder of a mixture of compounds of the following formula

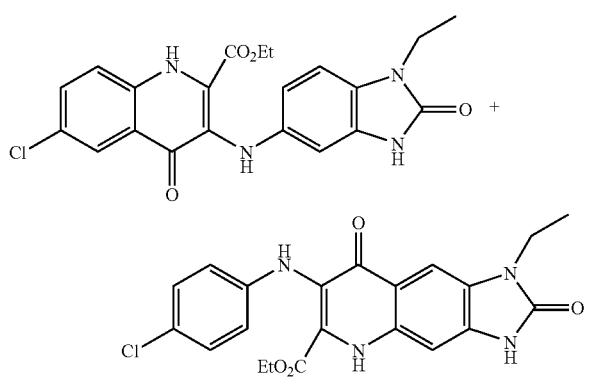

EXAMPLE 2e 470 parts of polyphosphoric acid (85% of $H_3PO_4$ content) and 47 parts of the product isolated in the example 1d are mixed in a reactor and gradually heated to 150° C. and stirred at this temperature for 4 hours. Then the reaction mixture is cooled to 60° C. and are added to 235 parts of wate. The suspension is filtered and washed with water. Drying under reduced pressure at 80° C. gives 41.6 parts of an orange powder of a compound of the following formula

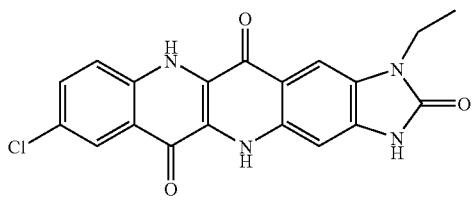

EXAMPLE 3a 103.1 parts of 2,3-dihydroxyfumaric acid dimethylester are suspended in 371 parts of methanol. 192.1 parts of 5-amino-benzimidazolo-2-one and 5 parts of concentrated HCl are added. The mixture is heated to reflux for 6 hours. The suspension is cooled to 5° C., and the precipitate is filtered off, washed with methanol and dried in vacuo at 60° C. to give 93.1 parts of a compound of the following formula

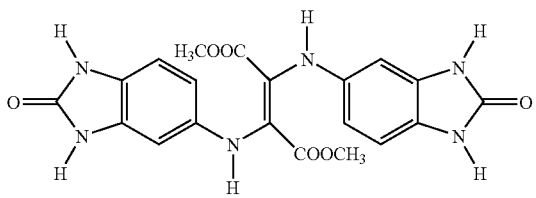

EXAMPLE 3b 278 parts of a mixture of biphenyl and diphenylether are heated to boiling, and a solution of 93.1 parts of the product of example 3a in 693 parts of a mixture of biphenyl and diphenylether at 130° C. are added within 30 minutes. The mixture is heated to 255° C. within 30 minutes, and cooled down to 50° C. The precipitate is filtered off, washed with petrol ether and dried in vacuo at 60° C. to give 73.7 parts of a compound of the following formula

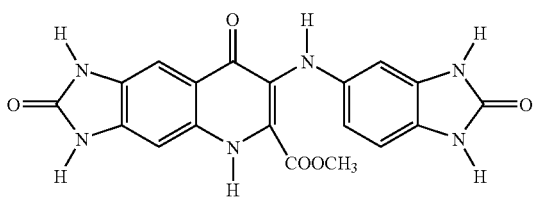

EXAMPLE 3c 73.7 parts of the product of example 3b are added to 535 parts of polyphosphoric acid at 145 to 150° C. and maintaine at 145 to 150° C. for 2 hours. The mixture was poured into 2500 parts of water at 0° C. The precipitate is filtered off, washed with water, and dried in vacuo at 60° C. to give 54.6 parts of a compound of the following formula

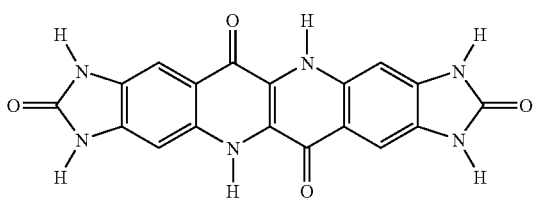

USE EXAMPLE 1

| | | |
|---|---|---|
| 4 | parts | of the pigment set out in the table below are milled in a ball mill with |
| 96 | parts | of a mixture of |
| 50 | parts | of a 60 per cent strength solution of co-aldehyde-melamine resin solution in butanol, |
| 10 | parts | of xylene and |
| 10 | parts | of ethylene glycol monoethyl ether for 24 hours. |

The resulting dispersion is sprayed onto sheet aluminium, left to dry in air for 30 minutes and then baked at 120° C. for 30 minutes. The result is a film of the colour specified in the table below, with very good migration fastness and also good light and weathering stability.

USE EXAMPLE 2

Example of the preparation of a 0.1% coloured PVC film (blend of colour pigment to white pigment 1:5):

| 16.5 | parts | of a plasticizer mixture consisting of equal parts of dioctyl phthalate and dibutyl phthalate are mixed with |
| 0.05 | parts | of the pigment set out in the table below and with |
| 0.25 | parts | of titanium dioxide. Then |
| 33.5 | parts | of polyvinyl chloride are added. |

The mixture is friction-rolled on a double-roll mill for 10 minutes, the resulting sheet being continually cut with a spatula and rolled together. In the roll mill, one roll is held at a temperature of 40° and the other at a temperature of 140°. The mixture is subsequently taken off in sheet form and pressed between two polished metal plates at 160° for 5 minutes. This gives a coloured PVC film of high brightness and very good migration and light fastness.

TABLE

| Pigment of Example | Colour in Use Example 1 | Colour in Use Example 2 |
|---|---|---|
| 1e | orange | orange |
| 2e | orange | orange |

What is claimed is:

1. An Epindolidione compound of the formula (I)

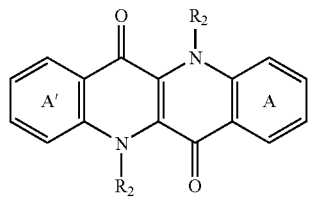

in which the nucleus designated A represents an annelated heteroaromatic ring system comprising an annelated ring which is fused on linearly, in 2,3-position, or angularly, in 1,2- or in 3,4-position, to feature the complementary member of moiety (1)

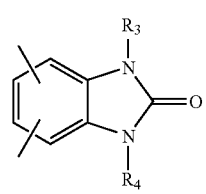

wherein
$R_3$ and $R_4$ are, independently, hydrogen, $C_{1-8}$alkyl, $C_{5-6}$cycloalkyl, benzyl, benzanilide or naphthyl whereby phenyl groups can be mono- or poly-substituted by radicals selected from the group consisting of halogen, nitro groups, $C_{1-8}$alkyl, phenyl, —COOR, with R being $C_{1-8}$alkyl and $C_{1-2}$alkoxy; or $R_3$ and/or $R_4$ are a radical of formula (a)

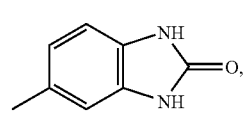

the nucleus A' represents a substituted or unsubstituted aromatic ring or an annelated heteroaromatic ring system comprising an annelated ring which is fused on linearly, in 2,3-position, or angularly, in 1,2- or in 3,4-position, to feature the complementary members of the moiety (12)

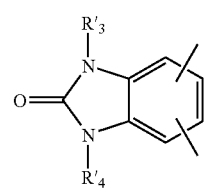

wherein $R'_3$ and $R'_4$ are, independently, hydrogen, $C_{1-8}$alkyl, $C_{5-6}$cycloalkyl, benzyl, benzanilide or naphthyl whereby phenyl groups can be mono- or poly-substituted by radicals selected from the group consisting of halogen, nitro groups, $C_{1-8}$alkyl, phenyl, —COOR with R being $C_{1-8}$ alkyl and $C_{1-2}$alkoxy, and $R_2$ is hydrogen, $C_{1-12}$alkyl or phenyl or —COOR, with R being $C_{1-8}$alkyl.

2. An Epindolidione compound of the formula (I')

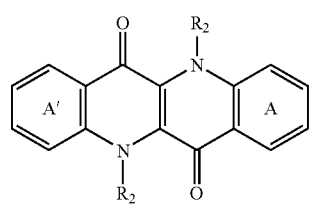

in which the nucleus designated A represents an annelated heteroaromatic ring system comprising an annelated ring which is fused on linearly, in 2,3-position, or angularly, in 1,2- or in 3,4-position, to feature the complementary member of moiety (1)

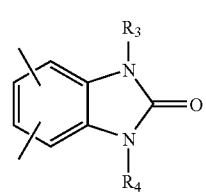

wherein

R₃ and R₄ are, independently, hydrogen, $C_{1-8}$alkyl, $C_{5-6}$cycloalkyl, benzyl, benzanilide or naphthyl whereby phenyl groups can be mono- or poly-substituted by radicals selected from the group consisting of halogen, nitro groups, $C_{1-8}$alkyl, phenyl, —COOR, with R being $C_{1-8}$alkyl and $C_{1-2}$alkoxy; or R₃ and/or R₄ are a radical of formula (a)

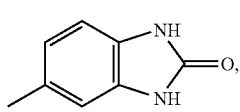

(a)

the nucleus A' represents a substituted or unsubstituted aromatic ring or an annelated heteroaromatic ring system comprising an annelated ring which is fused on linearly, in 2,3-position, or angularly, in 1,2- or in 3,4-position, to feature the complementary member of moiety (12)

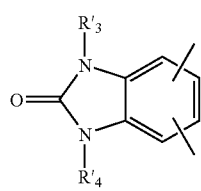

(12)

wherein R'₃ and R'₄ are, independently, $C_{1-8}$alkyl, $C_{5-6}$cycloalkyl, benzyl, benzanilide or naphthyl whereby phenyl groups can be mono- or poly-substituted by radicals selected from the group consisting of halogen, nitro groups, $C_{1-8}$alkyl, phenyl, —COOR, with R being $C_{1-8}$alkyl and $C_{1-12}$alkoxy, and R₂ is hydrogen, $C_{1-12}$alkyl or phenyl or —COOR, with R being $C_{1-8}$alkyl.

3. The compound according to claim 2 of the formulae (Ia), (IIa), (IIIa) and (IIIb)

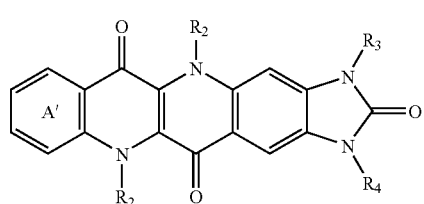

(Ia)

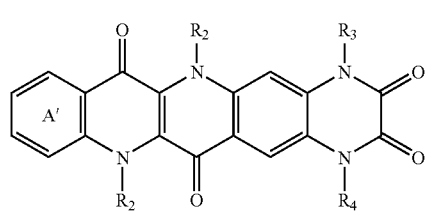

(IIa)

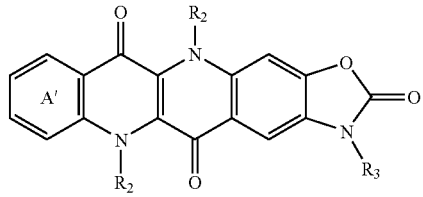

(IIIa)

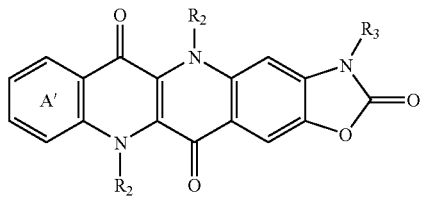

(IIIb)

in which A', R₃ and R₄ are defined as in claim 2.

4. The compound according to claim 3 of formula (Ib) and (IIb)

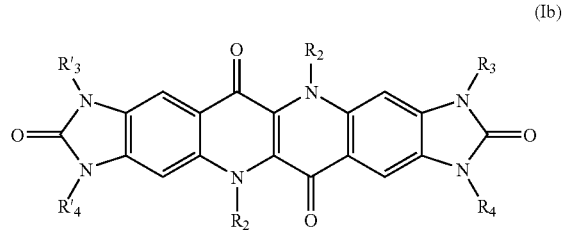

(Ib)

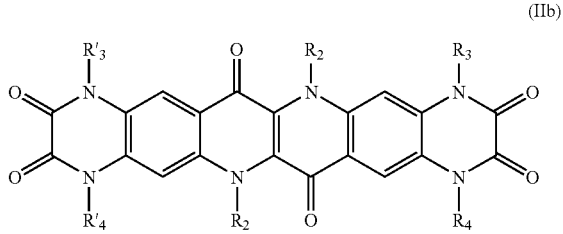

(IIb)

in which R₃, R₄, R'₃ and R'₄ are defined as in claim 2.

5. The compound according to claim 1 of formula (Id)

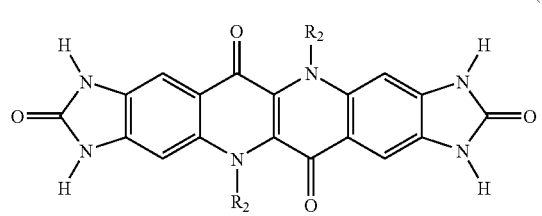

(Id)

wherein R₂ is defined as in claim 1.

6. Process for the preparation of epindolidione compound of the formula (I) according to claim 1 comprising the step of cyclizing a compound of the formula (VIII)

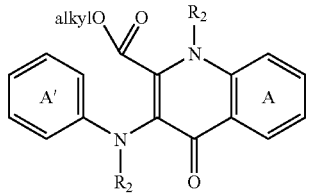

(VIII)

wherein A', $R_2$ and A have the meanings given in claim 1, in polyphosphoric acid or concentrated sulfuric acid.

7. A compound according to claim 1, wherein $R_3$ and $R_4$ are, independently, hydrogen, $C_{1-8}$alkyl, $C_{5-6}$cycloalkyl, benzyl, benzanilide or naphthyl whereby phenyl groups can be mono- or poly-substituted by radicals selected from the group consisting of chlorine, $C_{1-4}$alkyl, phenyl and —COOR, with R being $C_{1-8}$alkyl.

8. A compound according to claim 1, wherein $R'_3$ and $R'_4$ are, independently, hydrogen, $C_{1-8}$alkyl, $C_{5-6}$cycloalkyl, benzyl, benzanilide or naphthyl whereby phenyl groups can be mono- or poly-substituted by radicals selected from the group consisting of chlorine, $C_{1-4}$alkyl, phenyl and —COOR, with R being $C_{1-8}$alkyl.

9. A compound according to claim 2, wherein $R_3$ and $R_4$ are, independently, hydrogen, $C_{1-8}$alkyl, $C_{5-6}$cycloalkyl, benzyl, benzanilide or naphthyl whereby phenyl groups can be mono- or poly-substituted by radicals selected from the group consisting of chlorine, $C_{1-4}$alkyl, phenyl and —COOR, with R being $C_{1-8}$alkyl.

10. A compound according to claim 2. wherein $R'_3$ and $R'_4$ are, independently, $C_{1-8}$alkyl, $C_{5-6}$cycloalkyl, benzyl, benzanilide or naphthyl whereby phenyl groups can be mono- or poly-substituted by radicals selected from the group consisting of chlorine, $C_{1-4}$alkyl, phenyl and —COOR, with R being $C_{1-8}$ alkyl.

* * * * *